United States Patent
Gillinov et al.

(10) Patent No.: US 9,480,562 B2
(45) Date of Patent: *Nov. 1, 2016

(54) PRE-SIZED PROSTHETIC CHORDAE IMPLANTATION SYSTEM

(71) Applicant: THE CLEVELAND CLINIC FOUNDATION, Cleveland, OH (US)

(72) Inventors: A. Marc Gillinov, Orange Village, OH (US); Michael K. Banbury, Rockland, DE (US); Jeremy Hemingway, Cincinnati, OH (US); Craig B. Berky, Milford, OH (US); Jonathan Bauer, Cincinnati, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/890,308

(22) Filed: May 9, 2013

(65) Prior Publication Data

US 2014/0107769 A1 Apr. 17, 2014

Related U.S. Application Data

(63) Continuation of application No. 12/750,800, filed on Mar. 31, 2010, now Pat. No. 8,439,969.

(60) Provisional application No. 61/164,937, filed on Mar. 31, 2009.

(51) Int. Cl.
*A61F 2/24* (2006.01)
*A61B 17/064* (2006.01)

(52) U.S. Cl.
CPC ........... *A61F 2/2427* (2013.01); *A61F 2/2457* (2013.01); *A61F 2/2466* (2013.01); *A61B 17/0643* (2013.01)

(58) Field of Classification Search
CPC ............... A61F 2/2457; A61F 2/2487; A61B 17/0401; A61B 2017/00243
USPC ......... 606/151, 157, 220; 623/2.1, 2.12–2.19
See application file for complete search history.

(56) References Cited

U.S. PATENT DOCUMENTS

| 5,340,360 A | 8/1994 | Stefanchik |
| 7,083,636 B2 | 8/2006 | Kortenbach |
| 2003/0078653 A1 | 4/2003 | Vesely et al. |
| 2003/0105519 A1 | 6/2003 | Fasol et al. |

(Continued)

OTHER PUBLICATIONS

Falk et al., "How Does the Use of Polytetrafluoroethylene Neochordae for Posterior Mitral Valve Prolapse (Loop Technique) Compare with Leaflet Resection? A Prospective Radomized Trial", The Journal of Thoracic and Cardiovascular Surgery, Nov. 2008, 136: 1200-1206.

(Continued)

*Primary Examiner* — Katherine M Shi
(74) *Attorney, Agent, or Firm* — Tarolli, Sundheim, Covell & Tummino LLP

(57) ABSTRACT

A system includes a pre-sized prosthetic chordae, a papillary penetration member, and a female securing member. The pre-sized prosthetic chordae is directly connected to an attachment member. The papillary penetration member extends through both the chordae and the attachment member. The female securing member receives the penetration member. The penetration member is an axis about which the chordae pivot.

20 Claims, 10 Drawing Sheets

(56) References Cited

U.S. PATENT DOCUMENTS

| | | |
|---|---|---|
| 2004/0122512 A1 | 6/2004 | Navia et al. |
| 2004/0122513 A1 | 6/2004 | Navia et al. |
| 2004/0143323 A1 | 7/2004 | Chawla |
| 2004/0210303 A1 | 10/2004 | Sedransk |
| 2005/0075727 A1 | 4/2005 | Wheatley |
| 2006/0195182 A1 | 8/2006 | Navia et al. |
| 2006/0195183 A1 | 8/2006 | Navia et al. |
| 2006/0259135 A1 | 11/2006 | Navia et al. |
| 2006/0287716 A1* | 12/2006 | Banbury ............... A61F 2/2457 623/2.1 |
| 2007/0118151 A1* | 5/2007 | Davidson ......... A61B 17/00234 606/144 |
| 2007/0118154 A1 | 5/2007 | Crabtree |
| 2008/0149685 A1 | 6/2008 | Smith et al. |
| 2008/0195126 A1* | 8/2008 | Solem .......................... 606/155 |
| 2009/0088837 A1 | 4/2009 | Gillinov et al. |
| 2010/0249919 A1 | 9/2010 | Gillinov et al. |

OTHER PUBLICATIONS

Oppell et al., "Chordal Replacement for Both Minimally Invasive and Conventional Mitral Valve Surgery Using Premeasured Gore-Tex Loops", Ann Thorac Surg, 2000, 70: 2166-2168.

\* cited by examiner

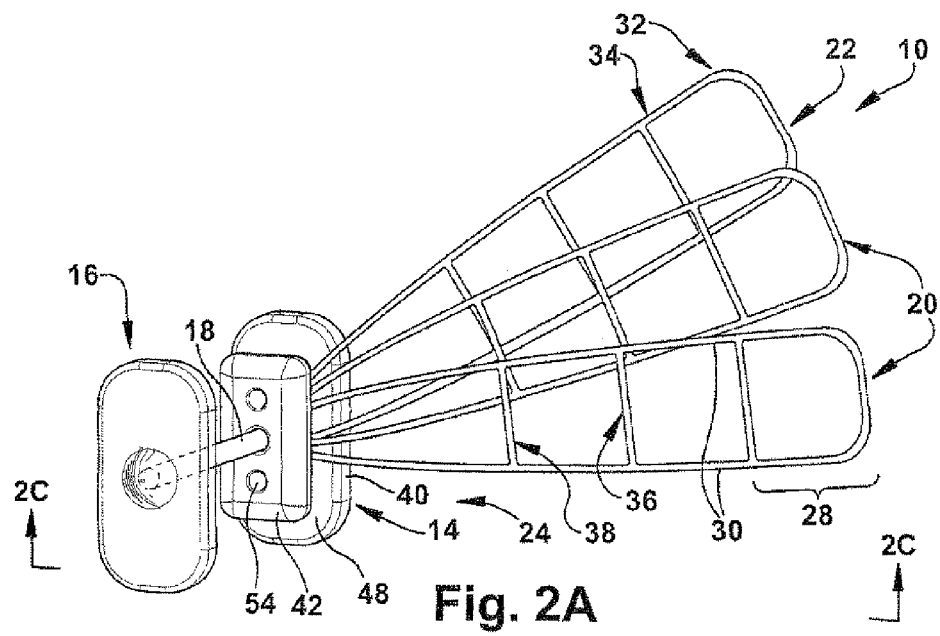
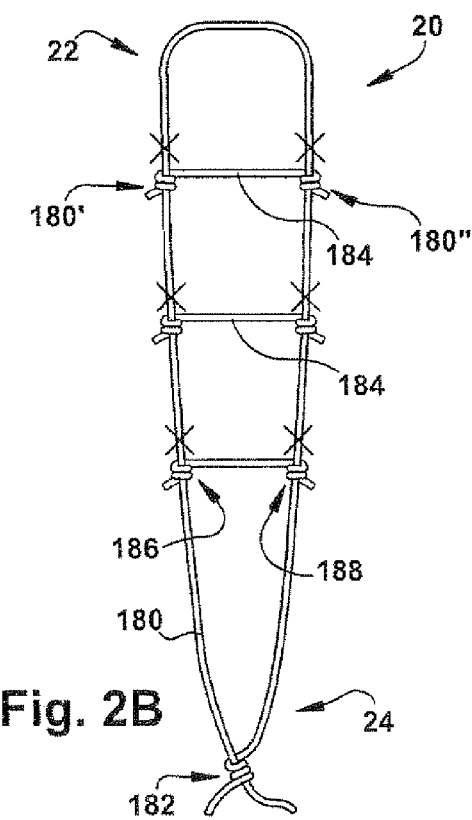

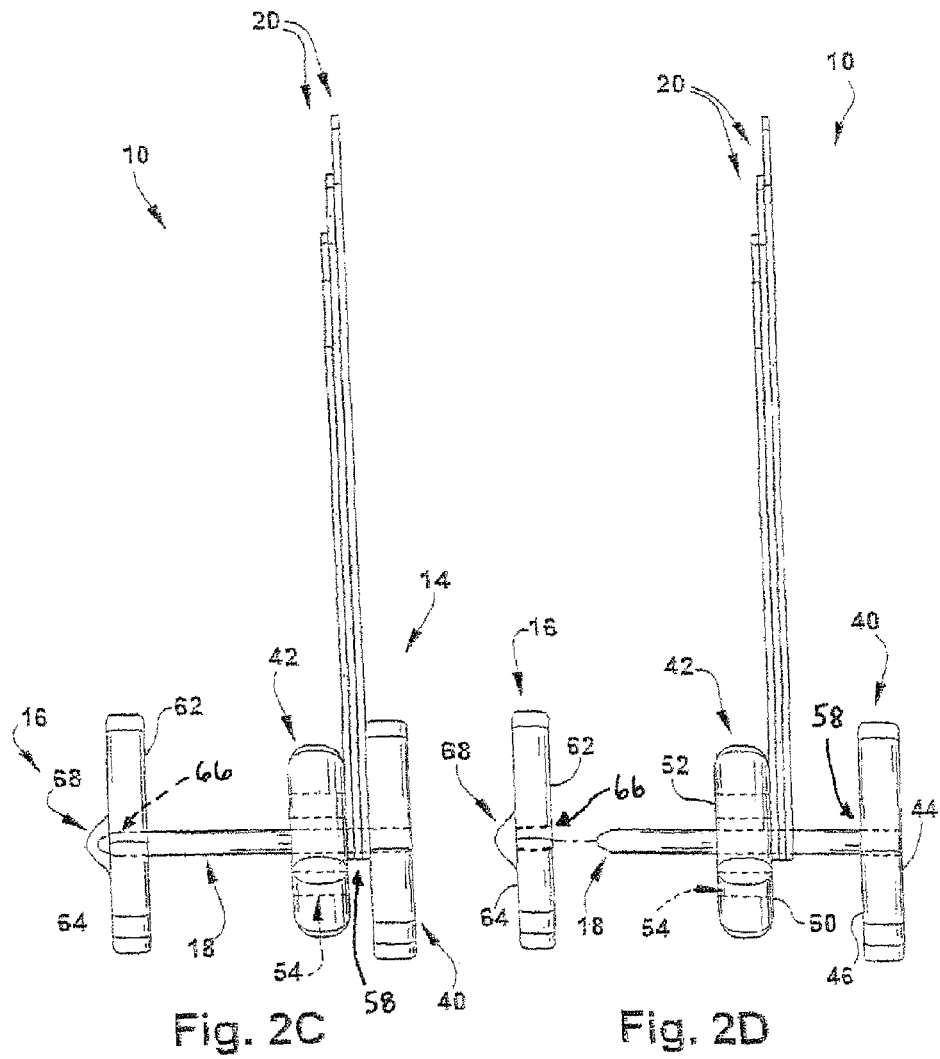

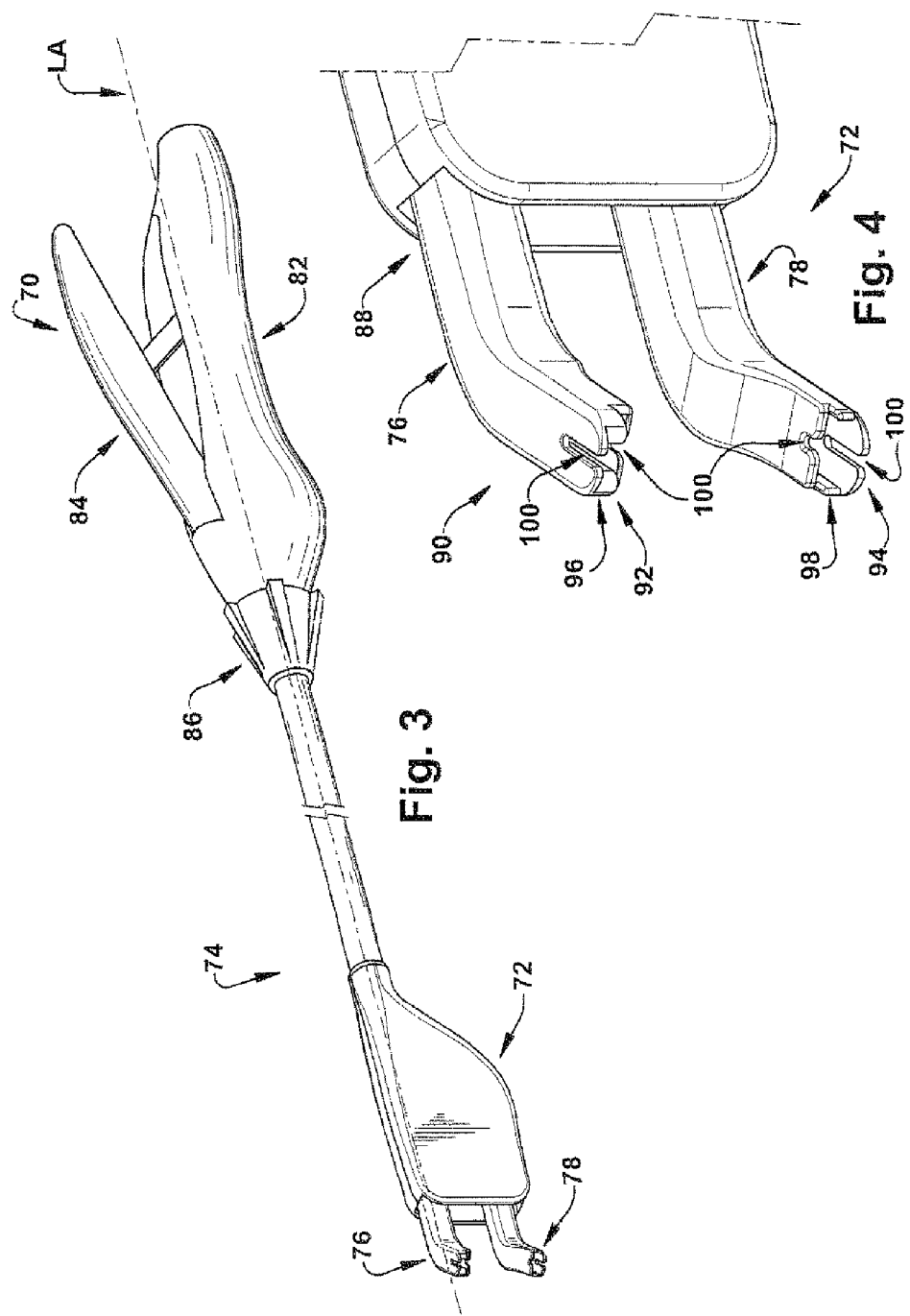

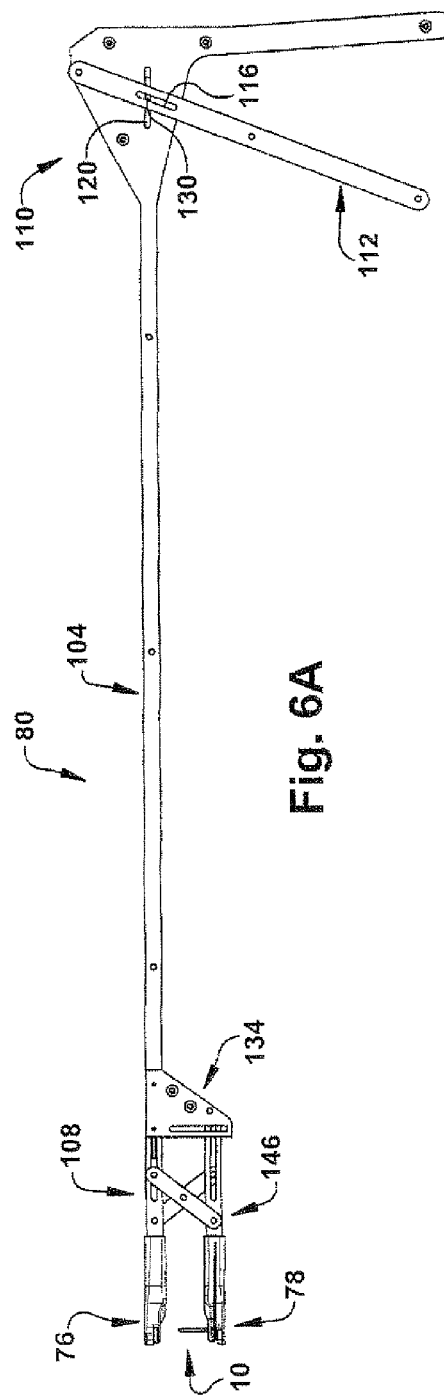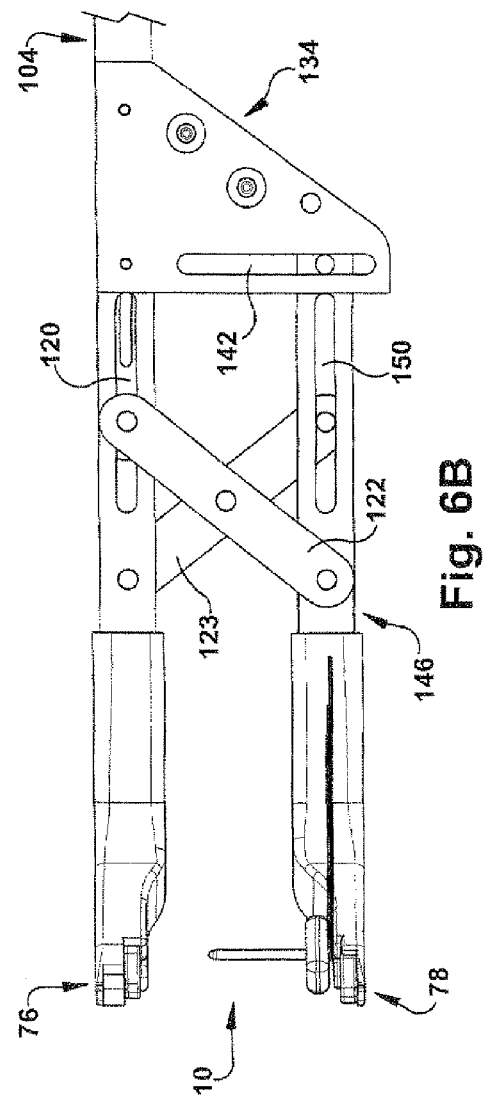
Fig. 6A
Fig. 6B

PRE-SIZED PROSTHETIC CHORDAE IMPLANTATION SYSTEM

RELATED APPLICATION

This application is a continuation of U.S. Ser. No. 12/750,800, filed Mar. 31, 2010, which claims priority from U.S. Provisional Patent Application Ser. No. 61/164,937, filed Mar. 31, 2009 (Now Expired). The subject matter of each of the aforementioned applications is hereby incorporated by reference in its entirety.

TECHNICAL FIELD

The present invention relates to cardiac valve repair, and more particularly to a pre-sized prosthetic chordae assembly (PCA) and apparatus for implanting the pre-sized PCA to repair mitral and tricuspid valves.

BACKGROUND OF THE INVENTION

Heart valve replacement is a well known procedure in which an artificial heart valve prosthesis is implanted in place of a diseased or malfunctioning heart valve. Heart valve prostheses may be mechanical or bioprosthetic. Use of mechanical valves typically requires extensive anticoagulation therapy. The need for anticoagulation therapy can be avoided in general by the use of artificial biological heart valves, such as bovine xenografts. Nevertheless, dystrophic calcification with subsequent degeneration is the major cause of failure of such bioprostheses in the long term.

When mitral or tricuspid valve replacement is performed, the chordae tendineae are cut, thus leaving the geometry and function of the ventricle impaired and in need of reconstruction. As an alternative to conventional heart valve replacement operations, diseased and malfunctioning chordae can be repaired by surgically replacing diseased heart chordae with artificial chordae. One known way of replacing a malfunctioning chordae uses a simple suture with a needle on each end of the suture. The suture is stitched through the papillary muscle and secured thereto with a knot. The two ends of the suture are then similarly stitched through the free ends of the valve leaflets.

Operations to repair heart valve chordae are technically demanding. For example, when a second knot is needed to secure the suture to the valve leaflets, the length of the suture spanning the distance between the papillary muscle and the valve leaflet is likely to change since there is nothing holding the suture in place. This complication increases the skill and time required to perform the procedure. Moreover, the valve will not function properly if the length of the artificial chordae between the papillary muscle and valve leaflet is overly long or overly short.

SUMMARY

One aspect of the present disclosure includes a system comprising a pre-sized prosthetic chordae, a papillary penetration member, and a female securing member. The pre-sized prosthetic chordae is directly connected to an attachment member. The papillary penetration member extends through both the chordae and the attachment member. The female securing member receives the penetration member. The penetration member is an axis about which the chordae pivot.

Another aspect of the present disclosure includes a system comprising a prosthetic chordae, an attachment member, a female securing member, and a papillary penetration member configured to pass through the attachment member, the chordae, and the securing member when implanted in a patient's heart. The penetration member is an axis about which the chordae pivot.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2A is an enlarged perspective view of the pre-sized PCA shown in FIG. 1A;

FIG. 2B is a perspective view showing a prosthetic chordae of the pre-sized PCA in FIG. 2A;

FIG. 2C is a cross-sectional view taken along Line 2C-2C in FIG. 2A;

FIG. 2D is a cross-sectional view showing the pre-sized PCA of FIG. 2C in an exploded configuration;

FIG. 3 is a perspective view showing an alternative configuration of the apparatus in FIG. 1B;

FIG. 4 is a magnified perspective view showing a distal applicator end of the apparatus in FIG. 1B;

FIG. 6A is a side view showing an actuating mechanism of the apparatus in FIG. 1B;

FIG. 6B is a magnified side view showing a distal end of the actuating mechanism in FIG. 6A;

DETAILED DESCRIPTION

Figure 1A:
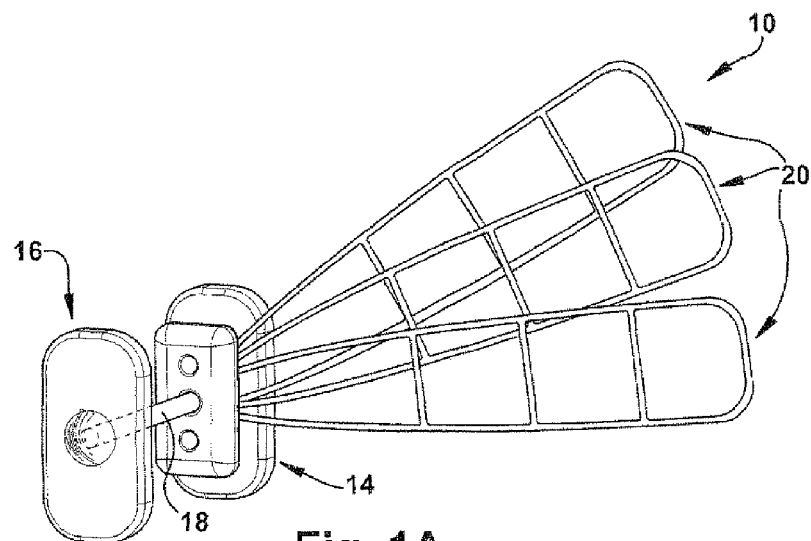
FIG. 1A is a perspective view of a pre-sized prosthetic chordae assembly (PCA) constructed in accordance with one aspect of the present invention.
Figure 1B:
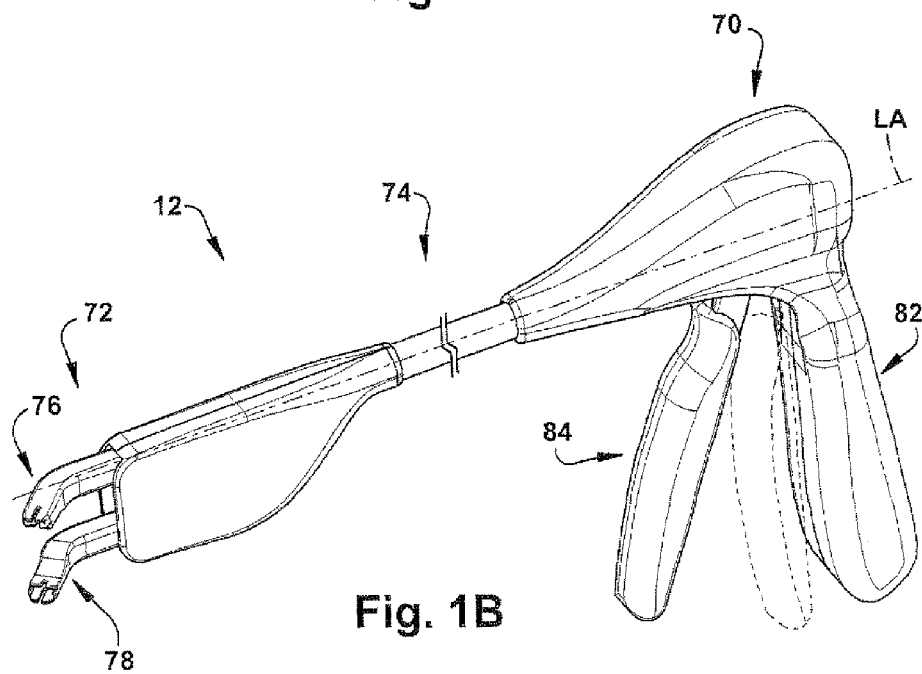
FIG. 1B is a perspective view of an apparatus for implanting the pre-sized PCA of FIG. 1A in a subject constructed in accordance with another aspect of the present invention.

The present invention relates to cardiac valve repair, and more particularly to a pre-sized prosthetic chordae assembly (PCA) and apparatus for implanting the pre-sized PCA to repair mitral and tricuspid valves. As representative of the present invention, FIGS. 1A-B illustrate a pre-sized PCA 10 (FIG. 1A) and an apparatus 12 (FIG. 1B) for implanting the pre-sized PCA in a subject. Although the present invention is described herein as being useful for treating a dysfunctional mitral valve (not shown), it should be appreciated that other cardiac valves, such as the tricuspid valve (not shown) are also treatable using the present invention.

Referring to FIGS. 2A-D, one aspect of the present invention includes a pre-sized PCA 10. As shown in FIG.

2A, the pre-sized PCA 10 comprises a male attachment unit 14 and a female securing member 16 for receiving a papillary muscle penetration member 18 of the male attachment unit. The male attachment unit 14 comprises a plurality of pre-sized prosthetic chordate 20 fixedly connected to at least one male attachment member.

The pre-sized prosthetic chordae 20 can be identically or similarly constructed as those described in U.S. patent application Ser. No. 12/238,322, filed Sep. 28, 2007, the entirety of which is hereby incorporated by reference.

As shown in FIG. 2A, each of the pre-sized prosthetic chordae 20 includes a first end portion 22, a second end portion 24, and a middle portion 26 extending between the first and second end portions. Each of the pre-sized prosthetic chordae 20 is comprised of a plurality of loop members 28 arranged in a daisy chain or ladder-like configuration. Each of the loop members 28 comprises two generally parallel strands 30 and includes first and second ends 32 and 34 respectively defining first and second arcuate junctions 36 and 38. The distance between the first and second arcuate junctions 36 and 38 is about 1 cm; however, it should be appreciated that the distance between the first and second arcuate junctions will depend upon anatomical variation between subjects. The two generally parallel strands 30 are fluidly connected to the first and second arcuate junctions 36 and 38 of each loop member 28. Each loop member 28 has a size and length that is substantially equal to the size and length of the other loop members.

FIG. 2B illustrates one example of a pre-sized prosthetic chordae 20 having a ladder-like configuration. In FIG. 2B, the pre-sized prosthetic chordate 20 can comprise a continuous first strand 180 of a material (e.g., a suture) having an arcuate first end portion 22 and a second end portion 24 that is formed into a knot 182. At least one rung 184 is axially-spaced between the first and second end portions 22 and 24 of the first strand 180. As shown in FIG. 2B, each of the rungs 184 includes first and second ends 186 and 188 that are securely connected to the first strand 180 by first and second knots 180' and 180". The rungs 184 can be made of any biocompatible material, such as suture material. During implantation of the pre-sized PCA 10, the first strand 180 can be cut at a plurality of points (indicated by "X") to quickly and easily adjust the length of the prosthetic chordae 20 so that the pre-sized PCA optimally conforms to the cardiac anatomy of the subject.

Each loop member 28 is made from a relatively elastic and flexible biocompatible material. Examples of such biocompatible materials can include Teflon and expanded polytetrafluoroethylene (ePTFE). ePTFE, for example, may be suture material or fabric material. Besides Teflon and ePTFE, it should be apparent to one skilled in the art that there are other suitable biocompatible materials, such as those frequently used to form sutures.

Each of the pre-sized prosthetic chordae 20 comprises an elongated, unitary unit of four interconnected loop members 28. Each of the pre-sized prosthetic chordae 20 is comprised of a single strand or fiber, such as a suture; however, it should be appreciated that the pre-sized prosthetic chordae may be comprised of multiple units, e.g., multiple sutures. Where each of the pre-sized prosthetic chordae 20 is comprised of multiple sutures, for example, each of the sutures can be fixedly joined to form each of the loop members 28. It should also be appreciated that any number of loop members 28 can be used to form the pre-sized prosthetic chordae 20. Accordingly, each of the pre-sized prosthetic chordae 20 is adjustable to a pre-determined length by adding or removing any desired number of loop members 28.

As noted above, the male attachment unit 14 comprises a plurality of pre-sized prosthetic chordate 20 fixedly connected to at least one male attachment member. In one aspect of present invention, each of the pre-sized prosthetic chordae 20 (FIG. 2A) is fixedly sandwiched between a first male attachment member 40 and a second male attachment member 42. The first male attachment member 40 comprises a pledget having first and second surfaces 44 and 46 (FIG. 2D). The first male attachment member 40 can be made of any medical grade material, such as a durable fibrous material (e.g., gauze) or polymer (e.g., ePTFE). As shown in FIG. 2A, the first male attachment member 40 additionally includes a rigid or semi-rigid backing 48 for supporting the papillary muscle penetration member 18. The backing 48 can be comprised of a hardened polymer, for example, that extends across all or a portion of the second surface 46 of the first male attachment member 40.

The second male attachment member 42 comprises a pledget having by first and second surfaces 50 and 52 (FIG. 2D). The second male attachment member 42 can be made of any medical grade material, such as a durable fibrous material (e.g., gauze) or polymer (e.g., ePTFE). The second male attachment member 42 includes at least one channel 54 (FIG. 2A) that extends between the first and second surfaces 50 and 52 and is capable of receiving the papillary muscle penetration member 18. As shown in FIG. 2D, each of the pre-sized prosthetic chordae 20 is securely attached to the first surface 50 of the second male attachment member 42 using sutures or clips (not shown), for example. It will be appreciated, however, that each of the pre-sized prosthetic chordae 20 may be securely attached to the second surface 52 of the first male attachment member 40.

Figure 9:
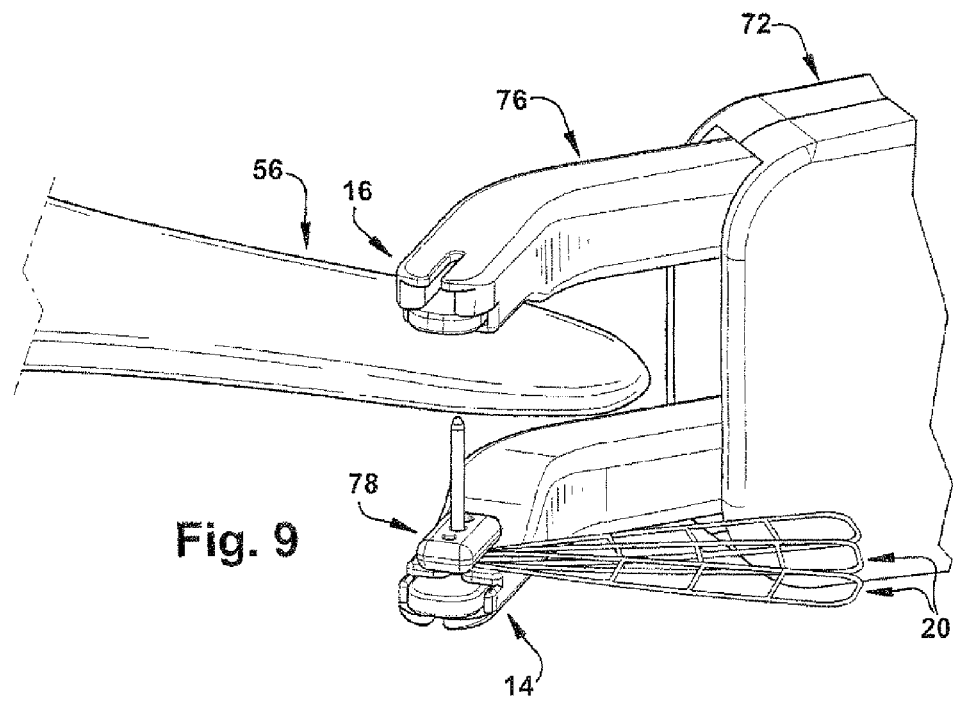
FIG. 9 is a perspective view showing the distal applicator end in FIG. 8 positioned about a papillary muscle.

As noted above, the male attachment unit 14 also includes a papillary muscle penetration member 18 for penetrating a papillary muscle 56 (FIG. 9). The papillary muscle penetration member 18 (FIG. 2D) can comprise a needle having a proximal end 58 and a sharpened distal tip 60. Where the papillary muscle penetration member 18 comprises a needle, the needle can have any desired gauge between 10 and 33. As shown in FIG. 2D, the proximal end 58 of the papillary muscle penetration member 18 is securely connected to the second surface 46 of the first male attachment member 40. It will be appreciated, however, that the proximal end 58 of the papillary muscle penetration member 18 can be disposed between the first and second surfaces 44 and 46 of the first male attachment member 40.

As shown in FIG. 2D, the female securing member 16 of the pre-sized PCA 10 comprises a pledget having by first and second surfaces 62 and 64. The female securing member 16 can be made of any suitable medical grade material, such as a durable fibrous material (e.g., gauze) or polymer (e.g., ePTFE). The female securing member 16 includes at least one channel 66 that extends between the first and second surfaces 62 and 64 and is capable of receiving the papillary muscle penetration member 18. The second surface 64 of the female securing member 16 also includes a protective member 68 to prevent the distal tip 60 of the papillary muscle penetration member 18 from damaging cardiac structures once the pre-sized PCA 10 is implanted. The protective member 68 can include a piece of cotton or gauze, for example, that is integrally formed with or securely attached to the second surface 64 of the female securing member 16. Alternatively, the protective member 68 can comprise a deformable backing that bubbles outward when the distal tip 60 of the papillary muscle penetration member 18 extends through the channel 66.

As shown in FIG. 1B and FIGS. 3-6B, another aspect of the present invention includes an apparatus 12 for implanting the pre-sized PCA 10 (FIG. 2A) in a subject. The apparatus 12 (FIG. 1B) comprises a proximal handle 70 operably linked to a distal applicator end 72 via an elongated intermediate portion 74. The elongated intermediate portion 74 defines a longitudinal axis LA that extends between the proximal handle 70 and the distal applicator end 72. The distal applicator end 72 of the apparatus 12 includes first and second jaw members 76 and 78 adapted to deliver the female securing member 16 (FIG. 2A) and the male attachment unit 14, respectively. As described in more detail below, an actuating mechanism 80 (FIG. 5) for actuating the second jaw member 78 (FIG. 1B) extends between the proximal handle 70 and the distal applicator end 72 of the apparatus 12.

Referring to FIG. 1B, the proximal handle 70 includes a handle member 82 that extends substantially perpendicular to the longitudinal axis LA and a lever 84. The lever 84 is movable from a first position to a second position (indicated by dashed line). Using tactile force, for example, movement of the lever 84 from the first position to the second position is used to operate the actuating mechanism 80 and thereby actuate the second jaw member 78.

It will be appreciated that the proximal handle 70 can have other configurations besides the one shown in FIG. 1B. As shown in FIG. 3, for example, the proximal handle 70 can be constructed so that both the handle member 82 and the lever 84 extend substantially parallel to the longitudinal axis LA of the apparatus 12. Additionally, the proximal handle 70 can include an adjustment mechanism 86 (e.g., a knob) to control rotation of the distal applicator end 72 about the longitudinal axis LA. For example, the adjustment mechanism 86 can be manipulated to cause the distal applicator end 72 to rotate in a clock-wise or counter-clockwise direction relative to the longitudinal axis LA to facilitate implantation of the pre-sized PCA 10.

As noted above, the distal applicator end 72 of the apparatus 12 includes opposable first and second jaw members 76 and 78 (FIG. 4). Each of the first and second jaw members 76 and 78 includes a proximal end 88 and a distal end 90. The distal end 90 of each of the first and second jaw members 76 and 78 includes first and second ports 92 and 94, respectively, for receiving the female securing member 16 (FIG. 2A) and the male attachment unit 14. Each of the first and second ports 92 and 94 (FIG. 4) is defined by first and second openings 96 and 98, each of which are in fluid communication with opposing longitudinal slots 100. The second opening 98 of the second jaw member 78 is adapted to receive the first male attachment member 40, and the first opening 96 of the first jaw member 76 is adapted to receive the female securing member 16. Each of the longitudinal slots 100 is adapted to receive the papillary muscle penetration member 18 and extends along a portion of the distal end 90 of the first and second jaw members 76 and 78.

Figure 5:
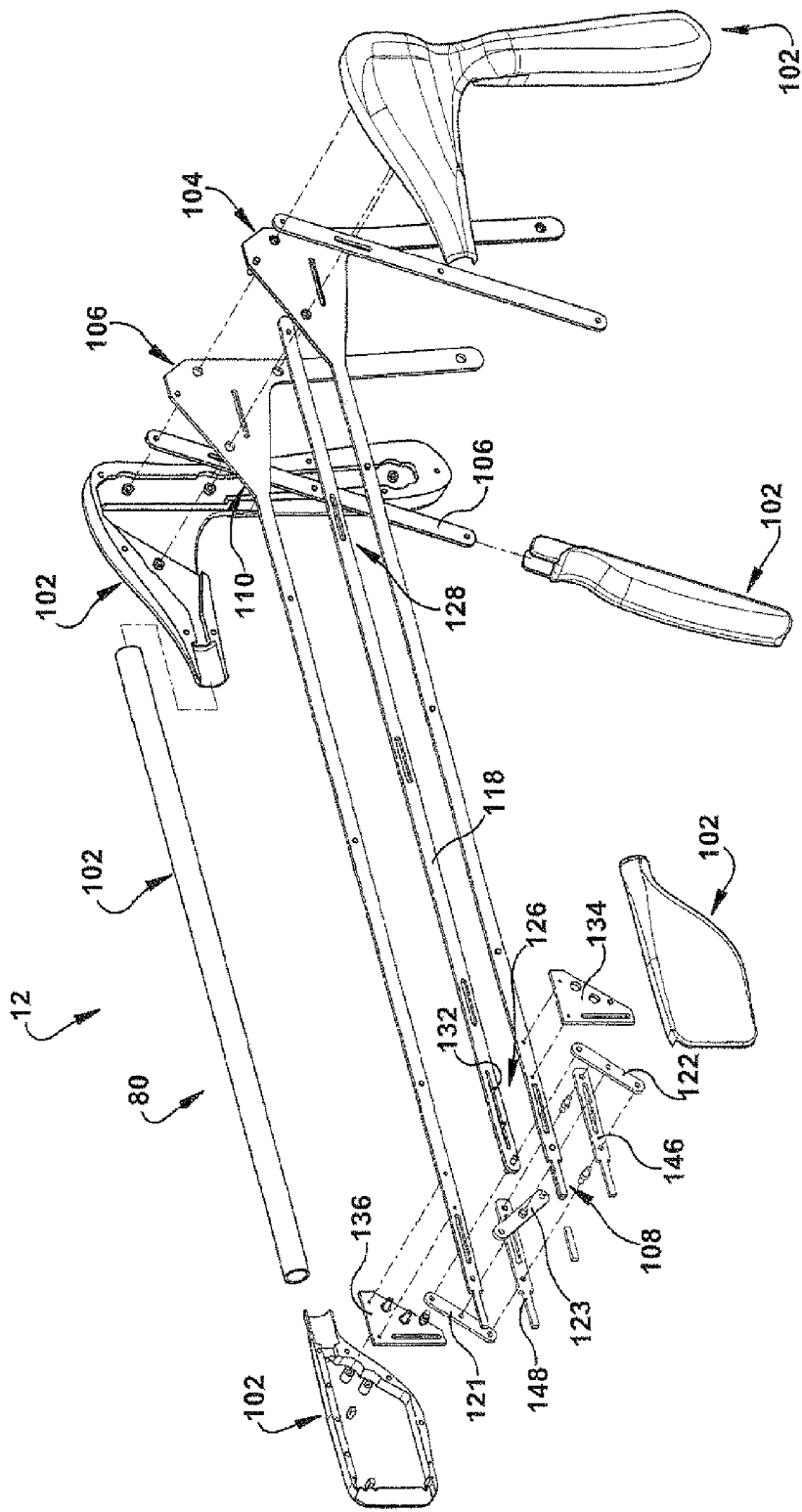
FIG. 5 is an exploded perspective view of the apparatus in FIG. 1B.

FIG. 5 is an exploded view of the apparatus 12 in FIG. 1B showing the components of the actuating mechanism 80, as well as multiple housing components 102 used to house the actuating mechanism. As shown in FIG. 5, the actuating mechanism 80 extends between the proximal handle 70 and the distal applicator end 72 of the apparatus 12. The actuating mechanism 80 comprises first and second L-shaped arm members 104 and 106, each of which has a proximal end 108 and a distal end 110. The proximal end 108 of each of the first and second L-shaped arm members 104 and 106 includes first and second lever arms 112 and 114, respectively, that form the movable lever 84 of the proximal handle 70. Additionally, the proximal end 108 of each of the first and second L-shaped arm members 104 and 106 includes a lateral slot 116 for operably connecting the first and second lever arms 112 and 114 with a control shaft 118.

The distal end 110 of the actuating mechanism 80 has a jack stand-like configuration. As shown in FIGS. 6A-B, the distal end 110 of each of the first and second L-shaped arm members 104 and 106 is adapted to securely mate with the first and second jaw members 76 and 78, respectively. Additionally, the distal end 110 of each of the first and second L-shaped arm members 104 and 106 includes a slot 120 (FIG. 6B) adapted to receive a first cross arm 122, a central cross arm 123, and a second cross arm 124.

The actuating mechanism 80 additionally comprises a control shaft 118 that is located between the first and second L-shaped arm members 104 and 106 and includes a proximal end 126 and a distal end 128. The proximal end 126 of the control shaft 118 includes a guide pin 130 capable of mating with the slot 120 of the first and second L-shaped arm members 104 and 106 and the lateral slot 116 (FIG. 6A) of the first and second lever arms 112 and 114. The distal end 128 of the control shaft 118 includes a plurality of pins 132 capable of mating with the first, central, and second cross arms 122, 123 and 124.

As shown in FIG. 5, the actuating mechanism 80 additionally includes wedge-shaped first and second plate members 134 and 136, each of which includes a first end 138 and a second end 140. The first end 138 of each of the first and second plate members 134 and 136 is capable of mating with the first and second L-shaped arm members 104 and 106, respectively. Each of the first and second plate members 134 and 136 includes an axial slot 142 extending between the first and second ends 138 and 140. The axial slot 142 of each of the first and second plate members 134 and 136 is capable of receiving a proximal end 144 of first and second distal elements 146 and 148. The proximal end 144 of each of the first and second distal elements 146 and 148 includes a laterally-extending slot 150 for mating with the central cross arm 123 (FIG. 6B).

Operation of the actuating mechanism 80 begins by depressing the movable lever 84. As the movable lever 84 is depressed, the first and second lever arms 112 and 114 progressively urge the guide pin 130 in a proximal direction so that the control shaft 118 moves laterally towards the proximal handle 70. As the control shaft 118 is moved laterally, the first and second cross arms 122 and 124 are pulled in a proximal direction along the slot 120 of each of the first and second L-shaped arm members 104 and 106. Movement of the first and second cross arms 122 and 124 causes the proximal end 144 of each of the first and second distal elements 146 and 148 to move axially towards the control shaft 118 along the axial slot 142 of each of the first and second plate members 134 and 136. Consequently, the first and second distal elements 146 and 148 cause the second jaw member 78 to move in an axial direction towards the first jaw member 76.

Figure 7:
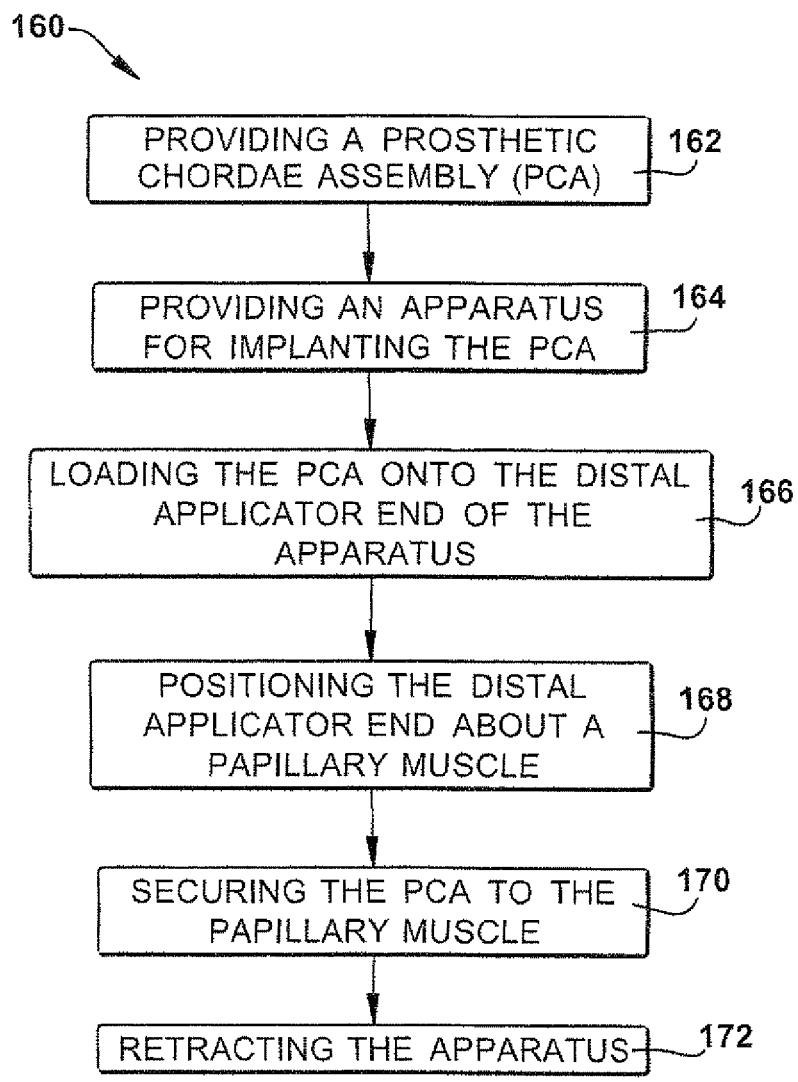
FIG. 7 is a process flow diagram illustrating a method for implanting a pre-sized PCA in a subject according to another aspect of the present invention.

FIG. 7 illustrates another aspect of the present invention. In FIG. 7, a method 160 is provided for implanting a pre-sized PCA 10 (FIG. 8) in a subject. The method 160 (FIG. 7) can be used to replace diseased or damaged native chordae (not shown). Disease or damage to native chordae can be caused by a variety of factors, such as infection, trauma, and old age. Disease or damage to the native chordae can rupture of the chordae and lead to valvular regurgitation (e.g., mitral valve regurgitation). Advantageously, the method 160 provides a simple and effective means for replacing damaged or diseased chordae to mitigate or prevent cardiac valve dysfunction.

Step 162 and Step 164 of the method 160 include providing a pre-sized PCA 10 and apparatus 12 for implanting the pre-sized PCA, respectively. The pre-sized PCA 10 can be substantially identical to the pre-sized PCA in FIGS. 2A-C, and the apparatus 12 can be substantially identical to the apparatus in FIG. 1B. Prior to replacing a diseased native chordae, the distance between a papillary muscle 56 (FIG. 9) and a location on a mitral valve leaflet (not shown) is first measured. Access to the native chordae may be obtained by open-heart surgery, for example. During surgery, the diseased native chordae are inspected to determine the size of the pre-sized prosthetic chordae 20 needed to replace the diseased native chordae. Generally, the size of the pre-sized prosthetic chordae 20 needed will depend on the size of the heart (not shown), as well as the implantation site.

A measuring device (not shown) is used to measure the distance between the papillary muscle 56 and the location on the mitral valve leaflet. For example, the measuring device can comprise a measuring device similar or identical to the measuring device disclosed in U.S. patent application Ser. No. 12/238,322. It will be appreciated that other types of measuring devices for measuring the distance between a papillary muscle 56 and a location on a cardiac valve leaflet are known in the art. After determining the distance between the papillary muscle 56 and the location on the mitral valve leaflet, the diseased native chordae are resected and an appropriately-sized PCA 10 selected for implantation.

Figure 8:
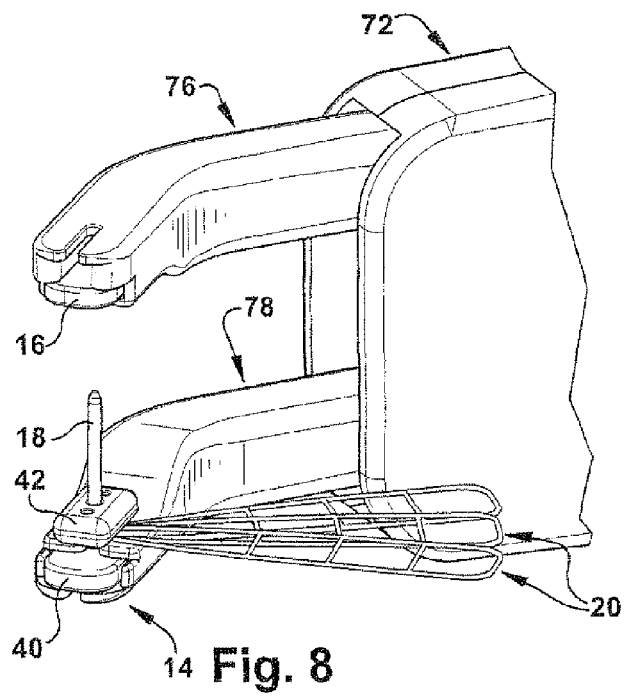
FIG. 8 is a perspective view showing the pre-sized PCA of FIG. 1A loaded onto the distal applicator end.

At Step 166, the pre-sized PCA 10 is loaded onto the distal applicator end 72 of the apparatus 12. As shown in FIG. 8, the male attachment unit 14 is mated with the second jaw member 78 by sliding the first male attachment member 40 and the papillary muscle penetration member 18 into the second opening 98 and the longitudinal slot 100, respectively. Additionally, the female securing member 16 is mated with the first jaw member 76 by sliding the female securing member into the first opening 96 of the first jaw member.

Once the pre-sized PCA 10 is loaded onto the distal applicator end 72, the distal applicator end is positioned about the papillary muscle 56 at Step 168. As shown in FIG. 9, the first and second jaw members 76 and 78 are disposed about opposite surfaces of the papillary muscle 56. Although the first and second jaw members 76 and 78 are shown in FIG. 9 as being positioned about the apical end of the papillary muscle 56, it will be appreciated that the first and second jaw members can be positioned about any other desired portion of the papillary muscle (e.g., the basal end).

Figure 10:
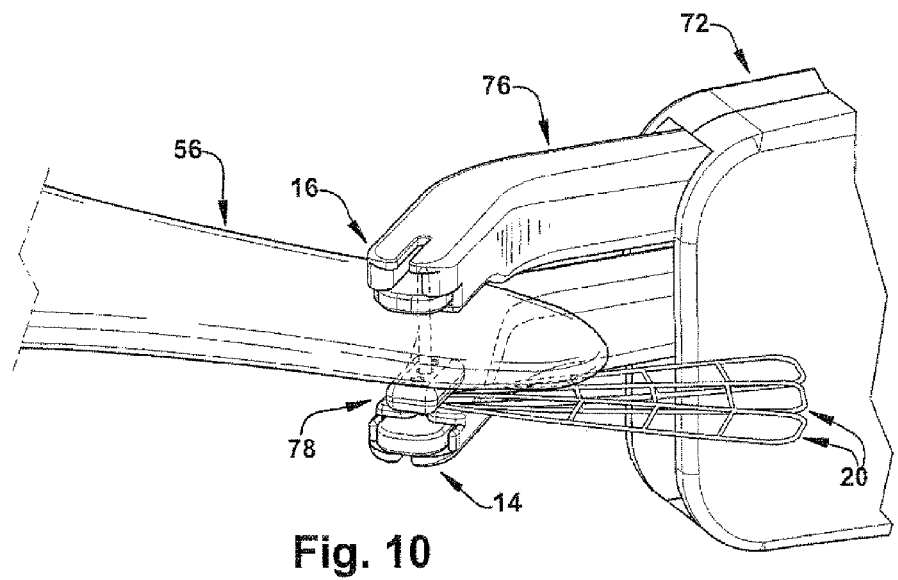
FIG. 10 is a perspective view showing the distal applicator end engaging the papillary muscle in FIG. 9.

With the first and second jaw members 76 and 78 correctly positioned about the papillary muscle 56, the pre-sized PCA 10 is then secured to the papillary muscle at Step 170. To secure the pre-sized PCA 10 to the papillary muscle 56, the movable lever 84 is depressed to actuate the second jaw member 78. As shown in FIG. 10, actuation of the second jaw member 78 causes the papillary muscle penetration member 18 to pierce the papillary muscle 56 and be driven into the female securing member 16. The lever 84 is depressed until the second jaw member 78 naturally stops and the distal tip 60 of the papillary muscle penetration member 18 is received by the female securing member 16.

Figure 11:
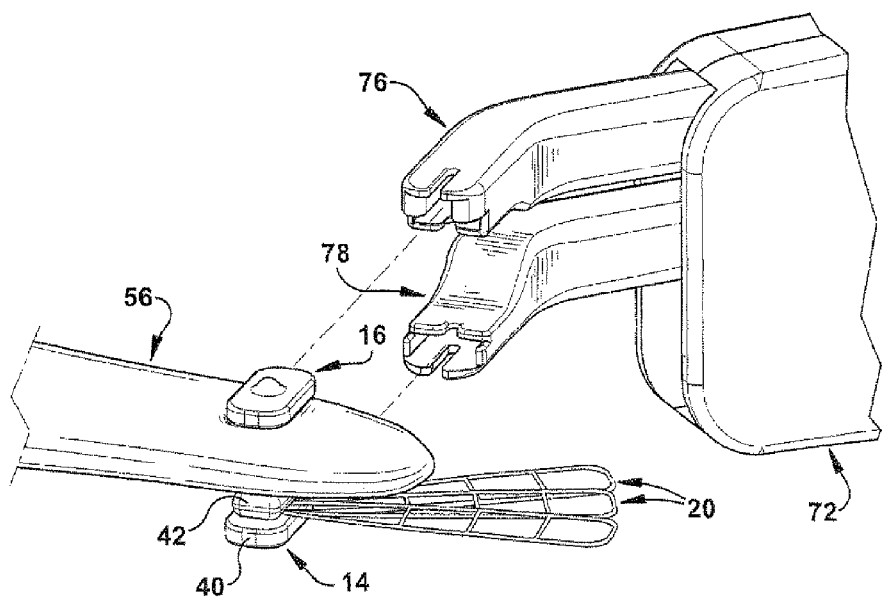
FIG. 11 is a perspective view showing the distal applicator end being retracted from the papillary muscle in FIG. 10.
Figure 12:
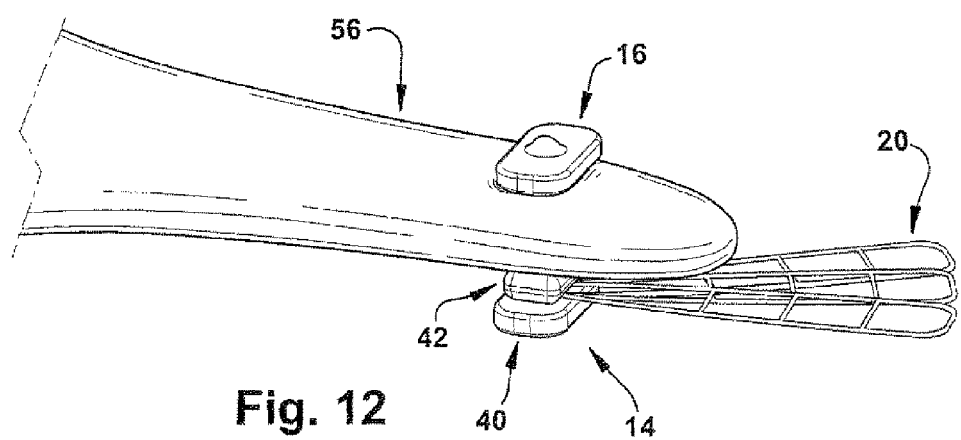
FIG. 12 is a perspective view showing the pre-sized PCA secured to the papillary muscle in FIG. 11.

Once the lever 84 is completely depressed, the distal applicator end 72 is retracted at Step 172. As shown in FIG. 11, the first and second openings 96 and 98 of the first and second jaw members 76 and 78 allows the female securing member 16 and the male attachment unit 14 to be slidably released from the distal applicator end 72, respectively, and remain affixed to the papillary muscle 56 (FIG. 12). After retracting the apparatus 12 from the subject's heart, each of the pre-sized prosthetic chordae 20 are securely attached to the mitral valve leaflet as described in U.S. patent application Ser. No. 12/238,322, for example. With the pre-sized PCA 10 implanted in the left ventricle (not shown), the mitral valve leaflet is pulled back into proper alignment so that the mitral valve can function properly and regurgitation through the valve is substantially reduced or prevented. Upon successful placement of the pre-sized PCA 10, effective valve function is verified (i.e., proper leaflet coaptation) and the open-heart surgery is completed.

From the above description of the invention, those skilled in the art will perceive improvements, changes and modifications. Such improvements, changes, and modifications are within the skill of the art and are intended to be covered by the appended claims.

The invention claimed is:

1. A system comprising:
   pre-sized prosthetic chordae directly connected to at least one attachment member;
   a papillary penetration member extending through both the chordae and the at least one attachment member; and
   a female securing member to receive the penetration member;
   wherein the penetration member includes an axis;
   wherein each of the chordae includes two elongated arms;
   wherein the chordae are configured to extend radially from, and substantially orthogonal to, the axis when the penetration member penetrates a papillary muscle.

2. The system of claim 1, wherein the penetration member includes a proximal end portion and a sharpened distal tip, the proximal end portion being directly connected to both the at least one attachment member and the chordae.

3. The system of claim 2 wherein the penetration member includes a needle.

4. The system of claim 1, wherein each of the chordae includes a plurality of short arms, which (a) are shorter than the elongated arms, and generally orthogonal to the elongated arms, and (b) connect the elongated arms to one another.

5. The system of claim 1, wherein the at least one attachment member includes a pledget.

6. The system of claim 5, wherein the female securing member includes an additional pledget.

7. The system of claim 1 comprising a deployment apparatus comprising first and second jaws spaced from one another to accommodate a width of the papillary muscle and deploy the penetration member through the papillary muscle.

8. The system of claim 1, wherein the at least one attachment member includes at least one of a rigid backing and a semi-rigid backing to support the penetration member.

9. The system of claim 1, wherein the at least one attachment member includes a channel and the penetration member extends through the channel.

10. A system comprising:
    prosthetic chordae;
    at least one attachment member including a channel;
    a female securing member; and
    a papillary penetration member configured to pass through the channel, the chordae, and the securing member when implanted in a patient's heart;

wherein the penetration member: (a) includes an axis; and (b) is configured to extend substantially orthogonal to the chordae when implanted in the patient's heart.

11. The system of claim 10, wherein the penetration member includes a proximal end and a sharpened distal tip.

12. The system of claim 11 wherein the penetration member includes a needle.

13. The system of claim 10, wherein each of the chordae includes two elongated arms.

14. The system of claim 13, wherein each of the chordae includes a plurality of short arms, which: (a) are shorter than the elongated arms, and generally orthogonal to the elongated arms, and (b) connect the elongated arms to one another.

15. The system of claim 10, wherein the female securing member and the at least one attachment member each include a pledget.

16. The system of claim 10 comprising a deployment apparatus comprising first and second jaws spaced from one another to accommodate a width of papillary muscle and deploy the penetration member through the papillary muscle.

17. The system of claim 16, wherein the penetration member is configured to pass from the first jaw and into the second jaw.

18. The system of claim 1, wherein the female securing member includes a protective member to prevent a distal tip of the penetration member from damaging cardiac structures once the system is implanted in the patient's heart.

19. A system comprising:
prosthetic chordae;
at least one attachment member including a channel;
a female securing member; and
a papillary penetration member configured to pass through the channel, the chordae, and the securing member when implanted in a patient's heart;
wherein the penetration member includes an axis;
wherein each of the chordae includes two elongated arms and a plurality of short arms that: (a) are shorter than and generally orthogonal to the elongated arms, and (b) connect the elongated arms to one another.

20. The system of claim 19 wherein:
the penetration member includes a needle; and
the female securing member and the at least one attachment member each include a pledget.

* * * * *